United States Patent [19]

Kobayashi et al.

[11] Patent Number: 5,789,616

[45] Date of Patent: Aug. 4, 1998

[54] METHOD FOR PRODUCTION OF ZINC ACRYLATE

[75] Inventors: Keiji Kobayashi; Yukihisa Kodama, both of Chiba; Minoru Saotome, Kanagawa; Yoshinori Saito, Chiba, all of Japan

[73] Assignees: Bridgestone Sports Co., Ltd; Nippon Shokubai Co., Ltd; Nihon Joyu Kogyo Co., Ltd., all of, Japan

[21] Appl. No.: 874,127

[22] Filed: Jun. 12, 1997

[51] Int. Cl.$^6$ ................................................. C07C 57/04
[52] U.S. Cl. ................................................. 562/598
[58] Field of Search ................................................. 562/598

[56] References Cited

U.S. PATENT DOCUMENTS 4,141,559  2/1979  Melvin et al. ............ 273/220
4,561,657  12/1985  Tominaga et al. ........ 273/218

FOREIGN PATENT DOCUMENTS 6009238  5/1985  Japan .

OTHER PUBLICATIONS

Japanese Patap. No.: 52–154436, Dec. 1977, Two Layer Golf Ball.
Japanese Patap. No.: 60–94434 May 1995, Rubber Composition for Golf Ball Core.
Japanaese Patap. No.: 2–218636, Aug. 1990, Production of Carbonyl Compound.
Japanese Patap. No.: 51–138616, Nov. 1976, Process for Preparing Zinc Acylate or Methacrylate.

*Primary Examiner*—Paul J. Killos
*Assistant Examiner*—Rosalynd Keys
*Attorney, Agent, or Firm*—Omri M. Behr, Esq.

[57] ABSTRACT

A method is provided for the production of zinc acrylate which possesses an essentially fine constitution, permits easy pulverization into a fine powder, and, when kneaded with a rubber composition, attains uniform diffusion in a state very rarely inducing fast adhesion or formation of cluster. The fine zinc acrylate powder is obtained by a method which comprises causing acrylic acid and a higher fatty acid of 12–30 carbon atoms to react with zinc oxide in an organic solvent while continuing dispersion of the zinc oxide in the organic solvent in the presence of an anionic surfactant.

8 Claims, 6 Drawing Sheets

METHOD FOR PRODUCTION OF ZINC ACRYLATE

BACKGROUND OF THE INVENTION

1. Field of the Invention

This invention relates to an improved method for the production of zinc acrylate. More particularly, it relates to an improved method for the production of zinc acrylate, the improvement being aimed at overcoming the various problems which arise when zinc acrylate is incorporated in and kneaded with a rubber composition or synthetic resin.

2. Description of the Prior Art

Zinc acrylate is a compound useful as a cross-linking agent. It is incorporated in a rubber composition for the purpose of improving the vulcanizing ability of the rubber composition or it is used as a modifier for a synthetic resin, for example.

As means for obtaining zinc acrylate, a method which comprises causing acrylic acid to react with a zinc compound in an organic solvent, distilling the reaction mixture thereby expelling the organic solvent therefrom, and then drying the residue of the distillation (JP-B-58-14,416) and a method which comprises filtering the reaction mixture mentioned above thereby removing the organic solvent and then drying the filtrate have been well known heretofore. These methods, however, suffer from poor workability and inferior yield because the reaction products thereof heavily adhere to the inner walls of their reaction vessels or the stirring vanes or they agglomerate into lumps and further incur the disadvantage that the repetition of these works results in breakage of the relevant devices. When the removal of the solvent is effected by reducing pressure, though the solvent contained in the formed zinc acrylate is scattered indeed, part of the zinc acrylate is simultaneously scattered to lower the yield. Further, the reduction of pressure is at a disadvantage in necessitating installation of extra devices for separation and recovery and consequently entailing a heavy economic loss.

As means for the solution of the problem mentioned above in the use of zinc acrylate as kneaded with a rubber composition, numerous methods have been proposed which basically comprise adding a higher fatty acid such as stearic acid or a zinc salt thereof to the mixture thereby coating the surface of zinc acrylate particles therewith (JP-A-52-154, 436, JP-A-53-83,834, JP-A-60-94,434, and JP-A-02-218, 639).

These methods, however, necessitate a step for the reaction of acrylic acid with a zinc compound and a step for coating the surface of zinc acrylate particles resulting from the reaction by adding a higher fatty acid such as stearic acid or a zinc salt thereof to the reaction mixture and consequently necessitate relevant devices fit for these steps. Further, when the zinc acrylate thus formed is kneaded with a rubber composition, it is required to be in the form of a fine powder having a particle size of not more than 325 mesh (44 µm), the zinc acrylate which is formed by the methods mentioned above must be pulverized into the fine powder. The pulverization into the fine powder not only demands huge labor but also proves disadvantageous in respect that the zinc acrylate during or after the work of pulverization is highly liable to emit dust and impair the work environment and give rise to hygienic problems. Further, since the mixture of the zinc acrylate with the rubber composition being formed during the kneading work adheres fast to the inner wall or the stirring vanes of the kneading device or agglomerates into clusters, it is liable to impair the workability of the kneading or disrupt the uniformity of diffusion of the fine powder. As a result, the pulverization is at a disadvantage in disrupting the homogeneity of the product ultimately obtained and bringing about an impairment of the quality thereof.

The method for the production of zinc acrylate heretofore adopted can hardly be called fully satisfactory particularly when the zinc acrylate obtained thereby is used as kneaded with a rubber composition.

An object of this invention, therefore, is to provide a method for the production of zinc acrylate such that the zinc acrylate obtained thereby possesses an essentially fine constitution, permits easy pulverization into a fine powder, and, when kneaded with a rubber composition, allows uniform and complete diffusion without appreciably inducing the phenomenon of either adhesion or agglomeration.

Another object of this invention is to provide a method for the production of zinc acrylate which fulfills the simplification of facilities of production attendant upon the rationalization of the process of production, prevents the phenomenon of adhesion or agglomeration, and precludes the emission of dust due to the work of handling.

SUMMARY OF THE INVENTION

We have made a diligent study in search of a method for the production of zinc acrylate with a view to accomplishing the objects mentioned above and, as a result, found that the zinc acrylate obtained by causing acrylic acid and a higher fatty acid to react with zinc oxide while continuing dispersion of the zinc oxide in an organic solvent in the presence of an anionic surfactant excels in the ability to inhibit the emission of dust during the work of handling the produced zinc acrylate.

To be specific, the objects mentioned above are accomplished by the following items (1)–(8).

(1) A method for the production of a fine zinc acrylate powder which comprises causing acrylic acid and a higher fatty acid of 12–30 carbon atoms to react with zinc oxide in an organic solvent while continuing dispersion of the zinc oxide in the organic solvent in the presence of an anionic surfactant.

(2) A method according to (1) above, wherein the higher fatty acid is added first for the reaction and the acrylic acid is then added for the reaction.

(3) A method according to (2) above, wherein the reaction mixture obtained by the reaction of acrylic acid with zinc oxide is deprived of the formed water and the organic solvent to dry.

(4) A method according to (1) above, wherein the amount of the anionic surfactant to be used is in the range of 0.03–1.5 parts by weight, based on 100 parts by weight of zinc oxide.

(5) A method according to (1) above, wherein the amount of the acrylic acid to be used is in the range of 100–250 parts by weight, based on 100 parts by weight of zinc oxide.

(6) A method according to (1) above, wherein the amount of the higher fatty acid to be added is in the range of 2–50 parts by weight, based on 100 parts by weight of zinc oxide.

(7) A method according to (6) above, wherein the higher fatty acid is stearic acid or palmitic acid.

(8) A method according to any of (1) to (7) above, therein the anionic surfactant is sodium dioctyl sulfosuccinate.

The zinc acrylate obtained by this invention, as compared with the product of any of the known methods mentioned above, permits easy division into a fine powder from its crystalline form and allow the clusters apparently formed in consequence of secondary agglomeration, for example, to be easily disintegrated and pulverized with a small force into a fine powder. Further, in the work of the pulverization and in the subsequent work of handling the resultant powder, the product of this invention prominently avoids emitting dust and enjoys excellent workability as compared with the product of any of the known methods mentioned above.

When the produced zinc acrylate is used as thermally kneaded with a rubber composition, for example, it is at an advantage in imparting an improved quality to the finished product because it induces neither adhesion nor agglomeration and yields thoroughly to polymerization with the rubber composition.

DESCRIPTION OF THE PREFERRED EMBODIMENT

Now, this invention will be described more specifically below.

The zinc oxide to be appropriately used in this invention may be a standard solid compound in a powdery state. Though it is preferred to be in a highly purified form, it may contain zinc hydroxide. As respects the amount of zinc oxide to be used, though the zinc oxide is generally used in the reaction in an equivalent weight stoichiometrically to the total weight of acrylic acid and a higher fatty acid, it suffices to adjust the amounts of acrylic acid and the higher fatty acid to be used so that the product may have a zinc acrylate content in the range of 80–98% by weight, preferably 85–95% by weight. When the zinc acrylate is used as a weight controller as when it is used for the core of a solid golf ball, for example, it may be safely used in an excess state so long as the excess amount causes a hindrance.

When the acrylic acid happens to be used in an excess amount, the excess acrylic acid may be expelled by distillation and then dried in conjunction with the organic solvent and the water formed by the reaction during the separation and recovery of the zinc acrylate as the reaction product.

The acrylic acid to be used in this invention is preferred to be in a form not diluted with water, though it tolerates inclusion of an insignificant amount of water. It can safely contain therein such a substance as, for example, hydroquinone or hydroquinone monomethyl ether which is generally used as a polymerization inhibitor. The amount of the acrylic acid to be used is in the range of 100–250 parts by weight, preferably 150–200 parts by weight, based on 100 parts by weight of the zinc oxide.

The higher fatty acid to be used in this invention is a fatty acid having 12–30 carbon atoms. As typical examples of the higher fatty acid, lauric acid, myristic acid, palmitic acid, stearic acid, behenic acid, oleic acid, and linoleic acid may be cited. These higher fatty acids may be used selectively in the form of a mixture. Among the higher fatty acids mentioned above, palmitic acid and stearic acid prove particularly favorable. The higher fatty acid may be used in its unmodified form or as dissolved in advance in the organic solvent or acrylic acid destined to be used in the reaction. The dissolution, when necessary, may be attained by application of heat.

The amount of the higher fatty acid mentioned above to be added is 2–50 parts by weight, preferably 10–35 parts by weight, based on 100 parts by weight of the zinc oxide. If the amount thus added is less than 2 parts by weight, the objects of this invention will not be fully accomplished because the zinc acrylate during or after the production is not easily fixed or diffused. If the amount exceeds 50 parts by weight, the excess higher fatty acid will produce an adverse effect of impairing the properties of the zinc acrylate. The optimum amount of addition is decided within the range of the purpose for which the zinc acrylate is used.

As typical examples of the anionic surfactant to be used in this invention, succinic dialkyl esters of sodium sulfonate such as alkylbenzene sodium sulfonate, secondary alcohol succinic half ester salts, alkyl sulfosuccinates, sodium diamyl sulfosuccinate, sodium dihexyl sulfosuccinate, sodium dioctyl sulfosuccinate, and monoethyl monododecyl sodium succinate, alkyl sulfates such as lauryl sulfate, tetradecyl sulfate, and oleyl sulfate, sulfuric sodium esters such as amide sulfonate and ricinoleic esters, α-sulfofatty alkyl ester salts, monosodium α-phosphorofatty esters, and sodium dialkyl phosphates. These anionic surfactants may be used selectively in the form of a mixture. Among other anionic surfactants enumerated above, sodium dioctyl sulfosuccinate proves particularly advantageous because it is capable of preventing the zinc acrylate during or after the production thereof from adhering to surfaces, forming clusters, and emitting dust. The amount of the anionic surfactant to be used is 0.03–1.5 parts by weight, preferably 0.1–1 part by weight, based on 100 parts by weight of zinc oxide. The anionic surfactant is generally used as mixed in advance with the organic solvent destined to be used in the reaction.

The organic solvent to be used in this invention is properly a hydrocarbon compound. As typical examples of the hydrocarbon compound, methanol, ethanol, isopropanol, benzene, toluene, xylene, n-hexane, and cyclohexane may be cited. Preferably, it is insoluble in water and is capable of forming an azeotropic mixture with water.

Now, a concrete preferred embodiment of this invention will be described below.

In a reaction vessel provided with a stirrer of a fully satisfactory stirring capacity and a thermal condenser, the organic solvent and the anionic surfactant are placed in prescribed amounts and kept stirred and the zinc oxide is added thereto and they are heated together to 10°–70° C., preferably 30°–50° C. The resultant suspension is kept at the temperature and the higher fatty acid is added thereto to form the zinc salt of the higher fatty acid. The time for the addition and the time for the reaction may be suitably selected in the range of 0.5–10 hours, preferably 1–5 hours, depending on the reaction temperature. Then, the reaction mixture is kept, when necessary by cooling, at 10°–70° C., preferably 15°–50° C., and the acrylic acid is added thereto to form zinc acrylate. The time for the addition and the time for the reaction may be suitably selected in the range of 0.5–10 hours, preferably 2–7 hours, depending on the reaction temperature. If the reaction temperature is lower than 10° C., the reaction velocity will be unduly low and the reaction will consume an unduly long time. Conversely, if the reaction temperature exceeds 70° C., the acrylic acid and the zinc acrylate will induce a polymerization reaction and the product will suffer degradation of quality.

The separation of the zinc acrylate for recovery after the reaction may be attained by separating the water formed by the reaction and the organic solvent through filtration from the interior of the reaction vessel and drying the zinc acrylate which remains after the filtration at a temperature of 10°–70° C. When the reaction vessel happens to be a kneader blender which is provided with a stirrer possessing scraping blades, the procedure of stirring the reaction mixture in its unmodified form and meanwhile distilling the reaction mixture at a temperature of 10°–70° C., preferably 15°–50° C., optionally under a reduced pressure to expel the excess acrylic acid, the organic solvent, and the water formed by the reaction and drying the residue of distillation proves a preferred embodiment permitting simplification of facilities and allowing efficiency of operation. The time for the distillation and the time for the drying may be suitably selected in the range of 1–20 hours, depending on the temperature. If the temperature of distillation and drying is lower than 10° C., the reaction will consume an unduly long time. Conversely, if the reaction temperature exceeds 70° C., the acrylic acid and the zinc acrylate will induce a polymerization reaction and the product will suffer degradation of quality. In this case, the expulsion of the water formed by the reaction and the organic solvent is preferred to resort to azeotropic distillation with water.

Now, this invention will be described more specifically below with reference to working examples. It should be noted, however, that this invention is not limited to these working examples.

EXAMPLE 1

In a jacketed kneader made of SUS-316, 10 liters in inner volume, 5,926 g of toluene as an organic solvent and 11.4 g of sodium dioctyl sulfosuccinate (produced by Kao Co., Ltd. and marketed under trademark designation of "Pellex OT-P") as an anionic surfactant were placed, then 1,411 g of zinc oxide was added thereto and stirred to be suspended therein and, with the internal temperature of the kneader kept at 40° C., a solution of 540 g of stearic acid as a higher fatty acid in 1,809 g of toluene was added to the stirred suspension over a period of one hour, and the suspension and the added solution were left reacting for 2 hours. Then, the internal temperature of the kneader was cooled to 15° C. and 2,362 g of acrylic acid was added to the reaction mixture therein gradually over a period of 3 hours so as to elevate the temperature to 35° C. and they were left reacting at 40° C. for 4 hours. The reaction mixture was gradually heated to 50° C. under a reduced pressure so as to allow the pressure to reach 20 Torrs and effect the expulsion of the water formed by the reaction and toluene by distillation over a period of 5 hours and obtain 3,988 g of zinc acrylate containing zinc stearate.

Figure 1:
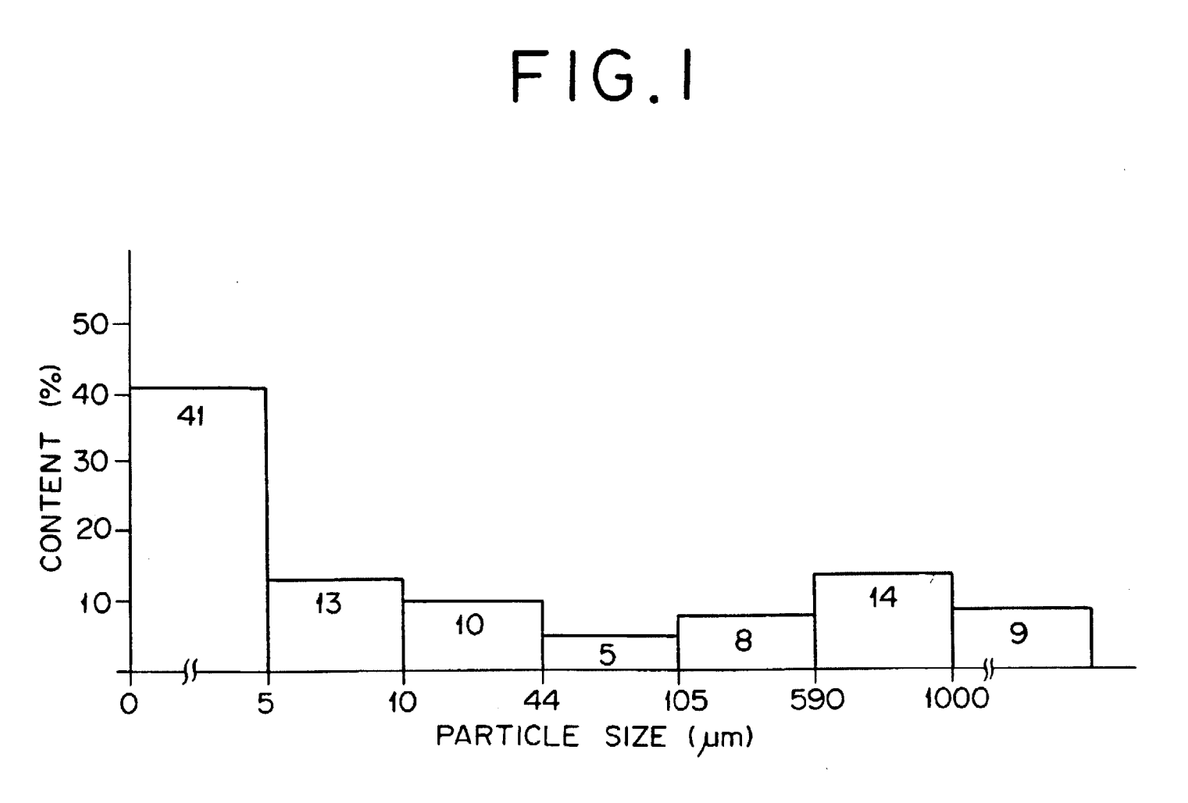
FIG. 1 is a diagram of the particle size distribution of zinc acrylate containing zinc stearate obtained in Example 1 of this invention.

The zinc acrylate consequently obtained was filtered with a sieve, 105 μm in size. The particles, less than 105 μm in particle size, were analyzed for particle size distribution by the laser diffraction particle size distribution testing method with a measuring instrument (produced by Nikkiso K.K. and marketed under trademark designation of "Microtrack FRA") using toluene as a solvent and the particles, not less than 105 μm in particle size, were analyzed similarly by the standard sieve wet shaking method with a measuring instrument, "Octagon 200," using toluene as a solvent. The results are shown in FIG. 1. It is clear from FIG. 1 that the zinc acrylate contained 64% by weight of particles of not more than 44 μm.

Then, the zinc acrylate was disintegrated and the resultant powder was filtered through a sieve, 105 μm in size. When 5 g of the particles which had passed the sieve were fallen onto a glass plate from a height of 50 cm, they produced a dust spread on the glass plate in a circle, 65 cm in radius. The dust which was emitted by the zinc acrylate during the disintegration was in a very small amount, though the particle size distribution diagram of FIG. 1 indicates the inclusion of a fine powder in a large proportion. The clusters partly formed in the zinc acrylate was readily collapsed.

The zinc acrylate was lightly pulverized. When 30 parts by weight of the particles, not more than 44 μm in particle size, and 100 parts by weight of polybutadiene rubber were kneaded and heated in a Bunbury mixer, they could be smoothly kneaded and neither adhered to the inner wall and the vanes of the Bunbury mixer nor produced any cluster.

EXAMPLE 2

3,845 g of Zinc acrylate, including zinc stearate was obtained by following the procedure of Example 1 while using 11.0 g of sodium dioctyl sulfosuccinate, 347 g of stearic acid dissolved in 1,216 g of toluene, and 2,411 g of acrylic acid instead.

Figure 2:
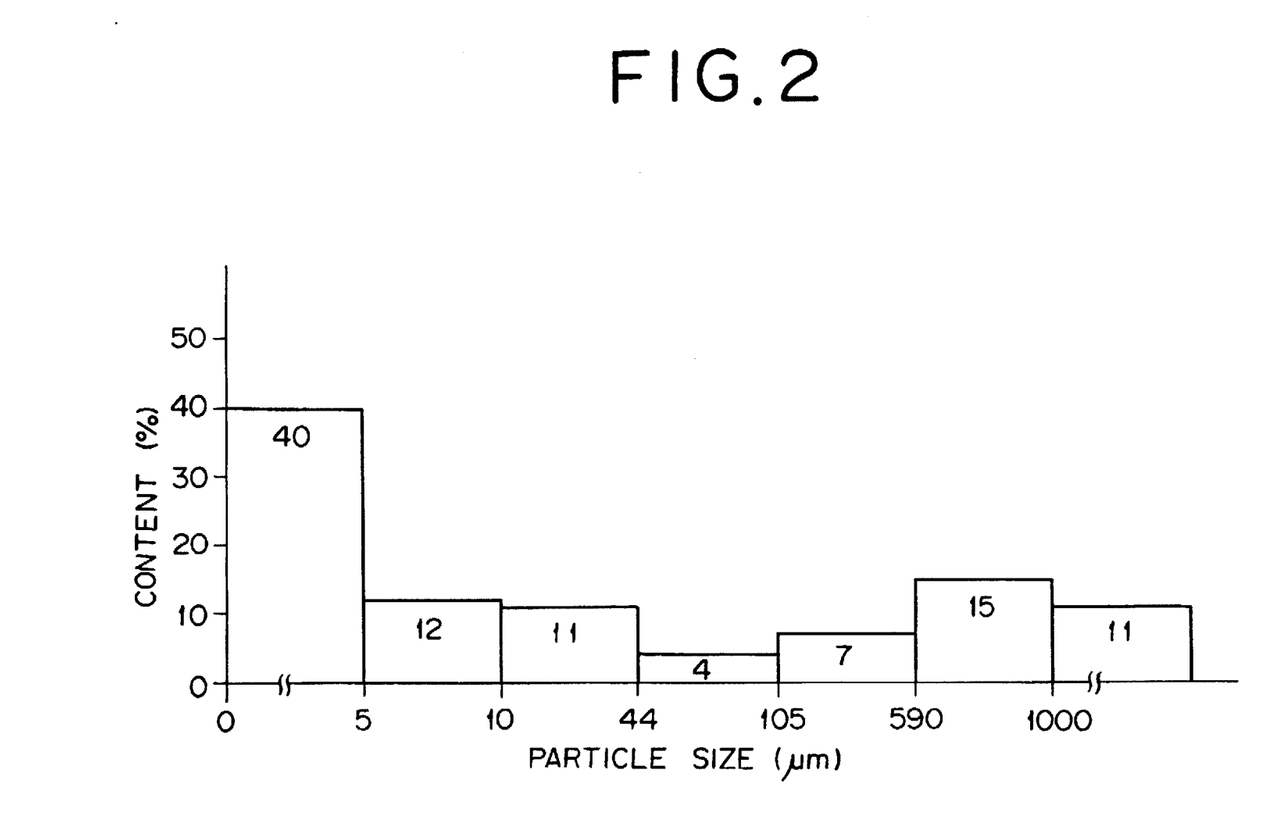
FIG. 2 is a diagram of the particle size distribution of zinc acrylate containing zinc stearate obtained in Example 2 of this invention.
Figure 3:
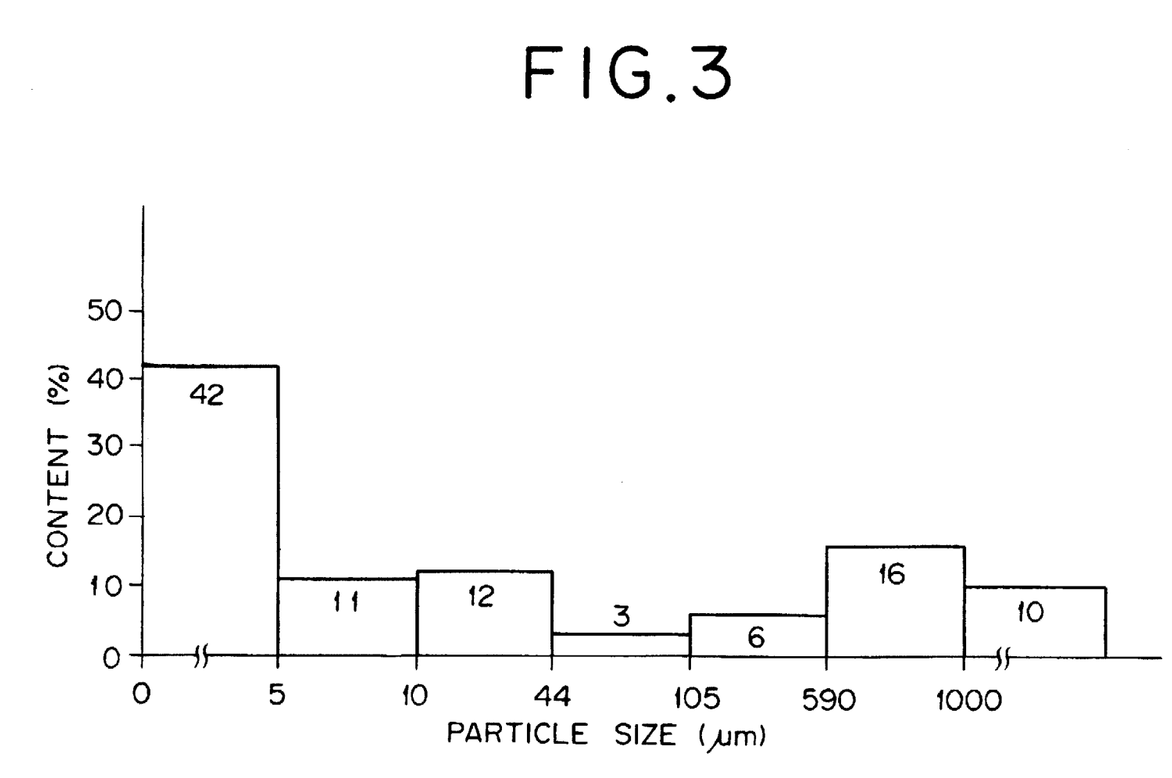
FIG. 3 is a diagram of the particle size distribution of zinc acrylate containing zinc stearate obtained in Example 3 of this invention.
Figure 4:
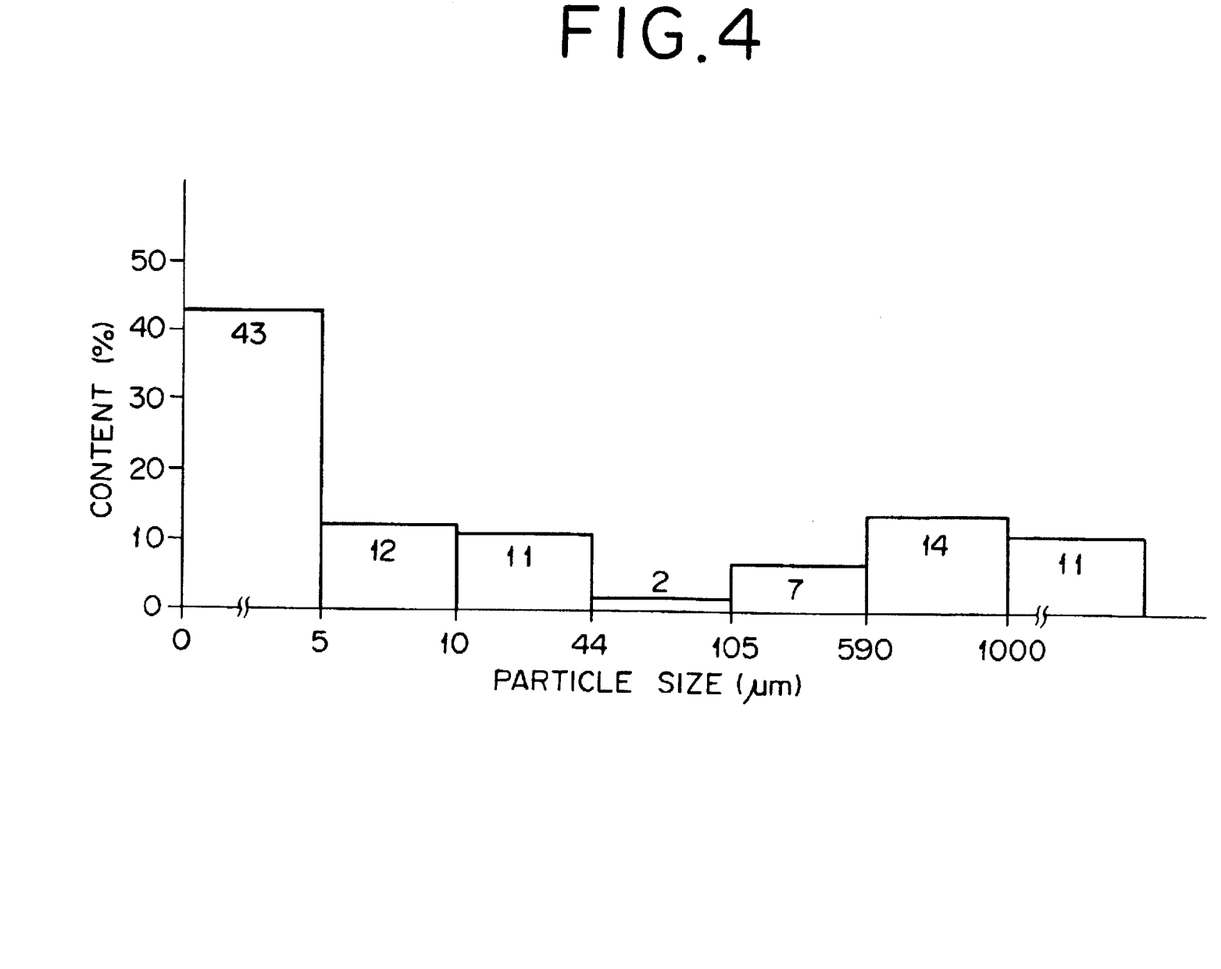
FIG. 4 is a diagram of the particle size distribution of zinc acrylate containing zinc palmitate obtained in Example 4 of this invention.

The produced zinc acrylate was analyzed for particle size distribution in the same manner as in Example 1. The results are shown in FIG. 2. It is noted from the diagram that the zinc acrylate contained 63% by weight of particles having a particle size of not more than 44 μm.

In the drop test, the zinc acrylate produced a circle of dust, 60 cm in radius. During the kneading under application of heat, the mixture neither adhered to the inner wall and the stirring vanes of the Bunbury mixer nor produced any discernible cluster.

EXAMPLE 3

3,712 g of Zinc acrylate, including zinc stearate was obtained by following the procedure of Example 1 while using 10.6 g of sodium dioctyl sulfosuccinate, 168 g of stearic acid dissolved in 588 g of toluene, and 2,456 g of acrylic acid instead.

The produced zinc acrylate was analyzed for particle size distribution in the same manner as in Example 1. The results are shown in FIG. 2. It is noted from the diagram that the zinc acrylate contained 65% by weight of particles having a particle size of not more than 44 μm.

In the drop test, the zinc acrylate produced a circle of dust, 63 cm in radius. During the kneading under application of heat, the mixture neither adhered to the inner wall and the stirring vanes of the Bunbury mixer nor produced any discernible cluster.

EXAMPLE 4

3,961 g of Zinc acrylate, including zinc stearate was obtained by following the procedure of Example 1 while using 546 g of palmitic acid dissolved in toluene in the place of stearic acid and using 2,345 g of acrylic acid.

The produced zinc acrylate was analyzed for particle size distribution in the same manner as in Example 1. The results are shown in FIG. 2. It is noted from the diagram that the zinc acrylate contained 66% by weight of particles having a particle size of not more than 44 µm.

In the drop test, the zinc acrylate produced a circle of dust, 62 cm in radius. During the kneading under application of heat, the mixture neither adhered to the inner wall and the stirring vanes of the Bunbury mixer nor produced any discernible cluster.

EXAMPLE 5

3,961 g of Zinc acrylate, including zinc stearate was obtained by following the procedure of Example 1 while using 0.6 g of sodium dioctyl sulfosuccinate.

Figure 5:
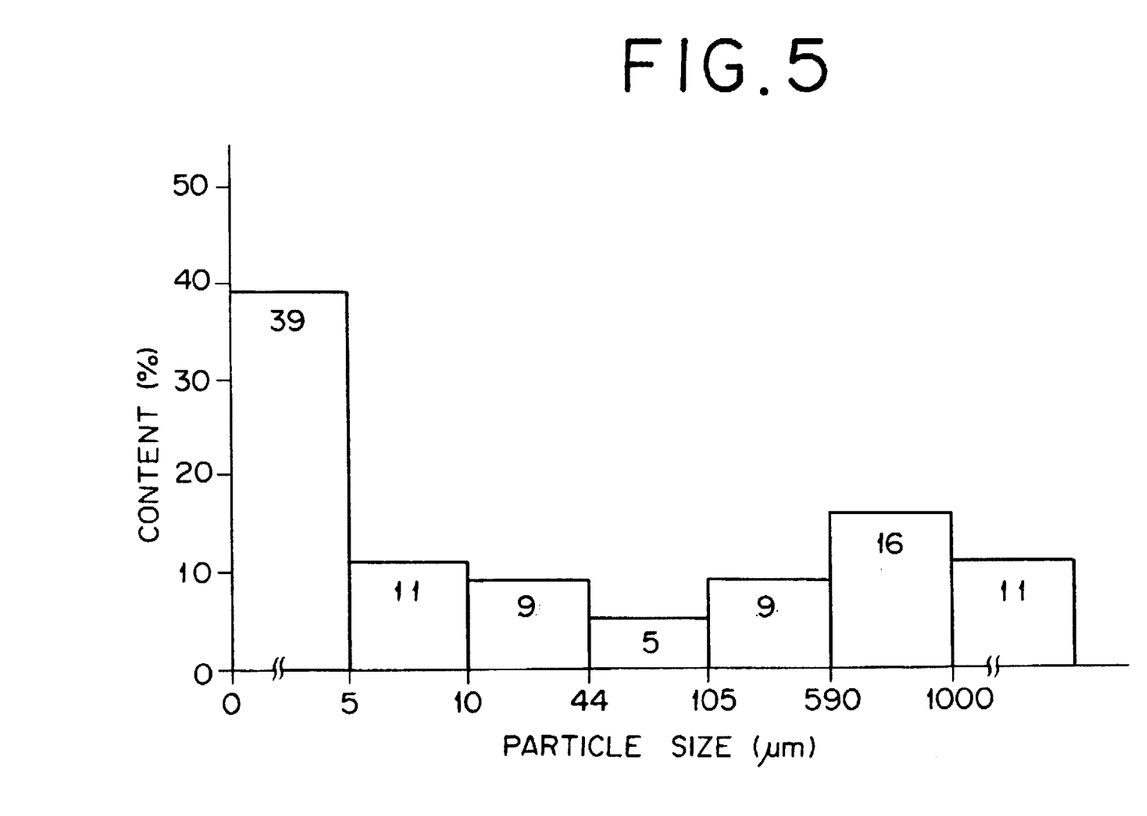
FIG. 5 is a diagram of the particle size distribution of zinc acrylate containing zinc palmitate obtained in Example 5 of this invention.
Figure 6:
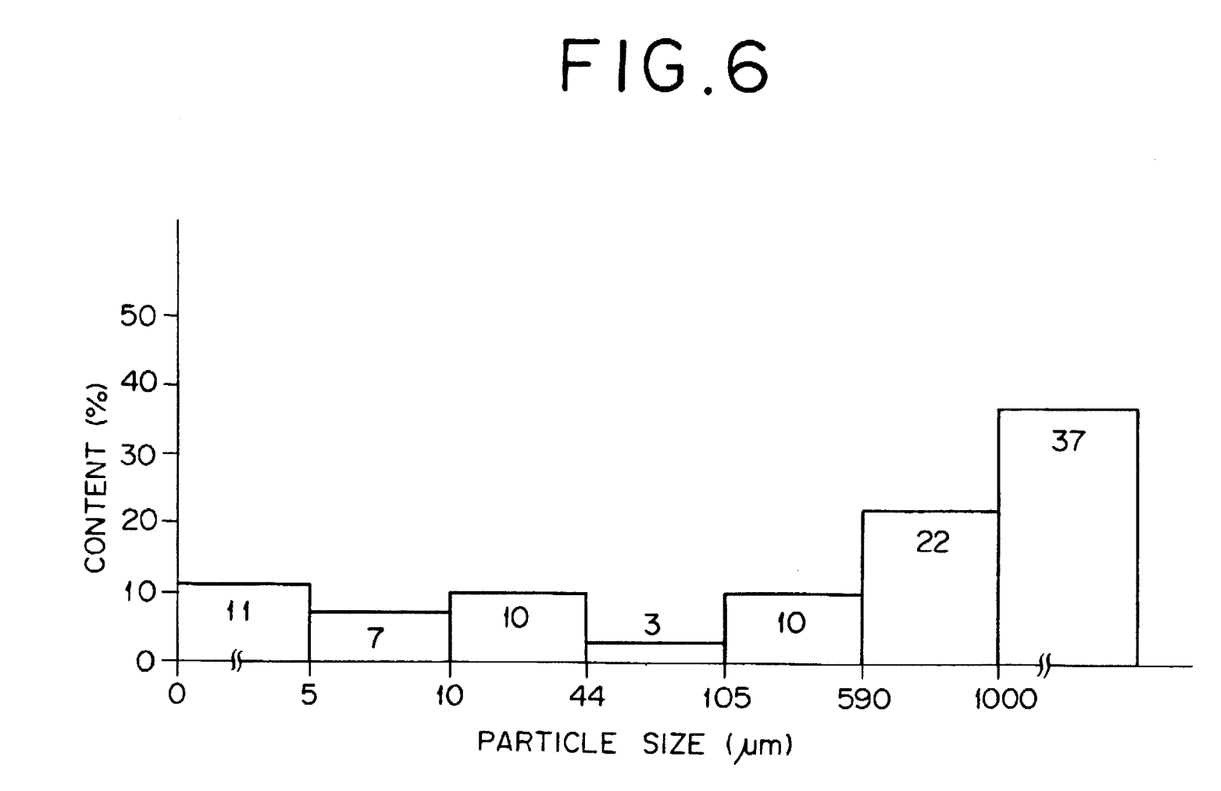
FIG. 6 is a diagram of the particle size distribution of zinc acrylate containing zinc stearate obtained in Control 1 of this invention.

The produced zinc acrylate was analyzed for particle size distribution in the same manner as in Example 1. The results are shown in FIG. 5. It is noted from the diagram that the zinc acrylate contained 59% by weight of particles having a particle size of not more than 44 µm.

In the drop test, the zinc acrylate produced a circle of dust, 69 cm in radius. During the kneading under application of heat, the mixture neither adhered to the inner wall and the stirring vanes of the Bunbury mixer nor produced any discernible cluster.

Control 1

3,900 g of Acrylic acid, was obtained by repeating the procedure of Example 1 while omitting the use of sodium dioctyl sulfosuccinate. During the production, adhesion of solid matter in a large amount was evident on the stirring vanes, which was a sign of poor workability.

The produced zinc acrylate was analyzed for particle size distribution in the same manner as in Example 1. The results are shown in FIG. 5. It is noted from the diagram that the zinc acrylate contained particles having a particle size of not more than 44 µm in as low a concentration as 28% by weight.

In the drop test, the zinc acrylate produced a circle of dust, 95 cm in radius. During the kneading under application of heat, the mixture clearly adhered to the inner wall and the stirring vanes of the Bunbury mixer and produced clusters.

These working examples clearly show that when the zinc salt of a higher fatty acid is first formed and the zinc salt of acrylic acid is subsequently formed in toluene as a solvent in the presence of sodium dioctyl sulfosuccinate as an anionic surfactant, this zinc salt is essentially a fine zinc acrylate powder which, in spite of the inclusion of minute particles in a large amount, emits dust only sparingly and which, even during the kneading under application of heat, neither adheres to the inner wall and the stirring vanes of the Bunbury mixer nor forms any cluster. It has been, consequently, confirmed that the presence of the anionic surfactant is useful for improving the surface condition of zinc acrylate to be produced.

What is claimed is:

1. A method for the production of a fine zinc acrylate powder which comprises causing acrylic acid and a higher fatty acid of 12–30 carbon atoms to react with zinc oxide in an organic solvent while continuing dispersion of said zinc oxide in said organic solvent in the presence of an anionic surfactant.

2. A method according to claim 1, wherein said higher fatty acid is added first for the reaction and said acrylic acid is then added for the reaction.

3. A method according to claim 2, wherein the reaction mixture obtained by said reaction of acrylic acid with zinc oxide is deprived of the formed water and said organic solvent to dry.

4. A method according to claim 1, wherein the amount of said anionic surfactant to be used is in the range of 0.03–1.5 parts by weight, based on 100 parts by weight of zinc oxide.

5. A method according to claim 1, wherein the amount of said acrylic acid to be used is in the range of 100–250 parts by weight, based on 100 parts by weight of zinc oxide.

6. A method according to claim 1, wherein the amount of said higher fatty acid to be added is in the range of 2–50 parts by weight, based on 100 parts by weight of zinc oxide.

7. A method according to claim 6, wherein said higher fatty acid is stearic acid or palmitic acid.

8. A method according to claim 1, wherein said anionic surfactant is sodium dioctyl sulfosuccinate.

* * * * *

UNITED STATES PATENT AND TRADEMARK OFFICE
CERTIFICATE OF CORRECTION

PATENT NO. : 5,789,616
DATED : August 4, 1998
INVENTOR(S) : Keiji Kobayashi, et. al.

It is certified that error appears in the above-identified patent and that said Letters Patent is hereby corrected as shown below:

Title page, item [73], Assignee: should read --Nihon Joryu Kogyo Co., Ltd.

Signed and Sealed this

Ninth Day of March, 1999

Attest:

Q. TODD DICKINSON

*Attesting Officer*  *Acting Commissioner of Patents and Trademarks*